(12) United States Patent
Srinivasan et al.

(10) Patent No.: US 10,224,715 B2
(45) Date of Patent: Mar. 5, 2019

(54) INTELLIGENT POWER ROUTING DEVICE

(71) Applicant: The John Hopkins University, Baltimore, MD (US)

(72) Inventors: Rengaswamy Srinivasan, Ellicott City, MD (US); Lakshminarayan Srinivasan, Oakland, CA (US)

(73) Assignee: The Johns Hopkins University, Baltimore, MD (US)

( * ) Notice: Subject to any disclaimer, the term of this patent is extended or adjusted under 35 U.S.C. 154(b) by 107 days.

(21) Appl. No.: 15/356,892

(22) Filed: Nov. 21, 2016

(65) Prior Publication Data

US 2018/0145506 A1    May 24, 2018

Related U.S. Application Data

(60) Provisional application No. 62/259,229, filed on Nov. 24, 2015.

(51) Int. Cl.
| | |
|---|---|
| *H02J 1/14* | (2006.01) |
| *G05B 19/048* | (2006.01) |
| *A61F 2/72* | (2006.01) |
| *A61F 2/74* | (2006.01) |
| *A61F 2/70* | (2006.01) |

(52) U.S. Cl.
CPC ............... *H02J 1/14* (2013.01); *A61F 2/72* (2013.01); *G05B 19/048* (2013.01); *A61F 2002/704* (2013.01); *A61F 2002/741* (2013.01); *G05B 2219/45172* (2013.01)

(58) Field of Classification Search
CPC ............. H02J 1/14; A61F 2/72; G05B 19/048
See application file for complete search history.

(56) References Cited

U.S. PATENT DOCUMENTS

| | | | |
|---|---|---|---|
| 9,748,765 B2 * | 8/2017 | Huang ..................... | H02J 1/00 |
| 2008/0024007 A1 * | 1/2008 | Budampati ............... | H02J 1/08 307/19 |
| 2008/0052544 A1 * | 2/2008 | Hsieh ........................ | H02J 1/14 713/300 |
| 2008/0176608 A1 * | 7/2008 | Budampati ........... | H04B 1/1615 455/572 |

(Continued)

*Primary Examiner* — Vincent H Tran
(74) *Attorney, Agent, or Firm* — Sung T. Kim (57) ABSTRACT

A power routing device includes processing circuitry configured to receive inputs from device monitors configured to determine load status information from a plurality of loads, power-source monitors configured to determine source status information from a plurality of power sources, and command modules configured to provide context information regarding the loads or the power sources. Some of the loads have different operational characteristics than others. Some of the power sources have different operational characteristics than others. The power routing device is operably coupled to power-source distribution hardware selectively operably coupling selected ones of the power sources to selected ones of the loads. The power routing device is configured to direct the power-source distribution hardware to define routing between the selected ones of the power sources and the selected ones of the loads based on the source status information, the load status information and the context information.

19 Claims, 7 Drawing Sheets

(56) References Cited

U.S. PATENT DOCUMENTS

2011/0309681 A1* 12/2011 Kamijima ............. H02J 7/0013
  307/66
2017/0271913 A1* 9/2017 Nasiri ................... H02J 7/0065
2017/0331325 A1* 11/2017 Ristau ....................... H02J 9/04

* cited by examiner

INTELLIGENT POWER ROUTING DEVICE

CROSS-REFERENCE TO RELATED APPLICATIONS

This application claims the benefit of U.S. Provisional Application No. 62/259,229 filed on Nov. 24, 2015, the entire contents of which are hereby incorporated herein by reference.

TECHNICAL FIELD

Some example embodiments of the present disclosure generally relate to power provision technology, and more specifically relate to employment of intelligent power routing devices to manage power delivered to loads based on balancing a number of source side, load side and intent related factors.

BACKGROUND

Some mechanical devices, such as actuated prosthetic limbs, include multiple components that require different levels of power in order to operate. In this regard, for example, various ones of the components inside the prosthetic limb may perform different operations and have different ranges of motion. Thus, individual components inside the device may also require varying amounts of power that correspond to different sets of operations. As an example, turning a robotic wrist requires different amounts of power depending upon whether the wrist is merely turning for repositioning purposes, or the wrist is turning to attempt to open a jar. Thus, the mechanical load may differ for different operations requiring essentially the same movement.

In healthy human physiology, the spatiotemporal distribution of power delivery (glucose and oxygen delivered by blood) for limb movements is dynamically controlled based on muscle demands by regulating arterial resistance. However, existing prototypes of actuated prosthetic limbs typically match power demands with a static type or location of source. In other words, a few power sources, each having a fixed power/energy density value, and targeted to power a specific part within the limb, are typically employed without any ability to define dynamic control, resulting in limited power routing capabilities to devices and systems that have complex and variable loading conditions.

BRIEF SUMMARY OF SOME EXAMPLES

In one example embodiment, a power routing system is provided. The power routing system includes a plurality of loads, a plurality of power sources, power-source distribution hardware selectively operably coupling selected ones of the power sources to selected ones of the loads, device monitors configured to determine load status information from the loads, power-source monitors configured to determine source status information from the power sources, command modules configured to provide context information regarding the loads or the power sources, and a power routing device. At least some of the loads have different operational characteristics than other ones of the loads. At least some of the power sources have different operational characteristics than other ones of the power sources. The power routing device is operably coupled to the command modules, the power-source monitors and the device monitors. The power routing device is configured to receive the source status information, the load status information and the context information and to direct the power-source distribution hardware to define routing between the selected ones of the power sources and the selected ones of the loads based on the source status information, the load status information and the context information.

In another example embodiment, a power routing device is provided. The power routing device includes processing circuitry configured to receive inputs from device monitors configured to determine load status information from a plurality of loads, power-source monitors configured to determine source status information from a plurality of power sources, and command modules configured to provide context information regarding the loads or the power sources. At least some of the loads have different operational characteristics than other ones of the loads. At least some of the power sources have different operational characteristics than other ones of the power sources. The power routing device is operably coupled to power-source distribution hardware selectively operably coupling selected ones of the power sources to selected ones of the loads. The power routing device is configured to direct the power-source distribution hardware to define routing between the selected ones of the power sources and the selected ones of the loads based on the source status information, the load status information and the context information.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to software, hardware, firmware, or a combination thereof. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

As indicated above, some example embodiments may enable the provision of a mechanism by which to dynamically and intelligently route power to variable loads from power sources of different types and at different locations. An example embodiment will be described herein within the context of its application to powering a prosthetic device. In this context, example embodiments may be applicable to functional electrical stimulation (FES) used to contract muscle in paresis or paralysis. However, it should be appreciated that example embodiments may have broader applicability to other types of automated devices, autonomous instruments, machines, robots, and even to collections of devices where power control can be managed relative to power provision from different types of sources.

Some example embodiments may enable the provision of a device or system that is capable of providing dynamic and efficient power sourcing to devices that have spatiotemporally varying power demands. In this regard, for example, some example embodiments provide an intelligent power routing device that coordinates the dynamic coupling of power sources of various types and/or locations to dynamic loads. In some cases, the intelligent power routing device employs one or more power source controllers to proactively coordinate power sourcing between various locations and types by predicting usage patterns over various timescales (e.g., milliseconds, seconds, minutes, etc.) based on previous and ongoing inputs from microcontrollers and sensors involved in planning, executing and monitoring power needs.

Figure 1:
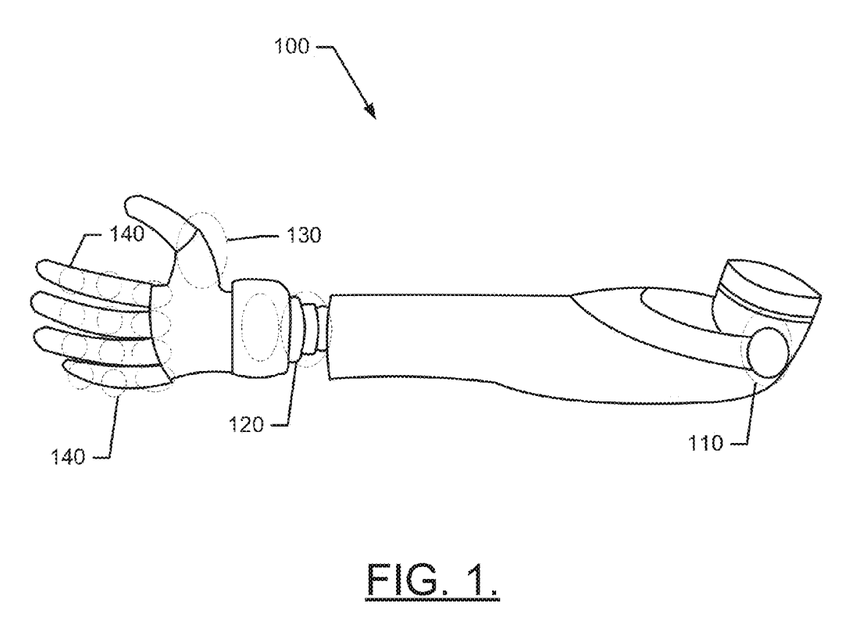
FIG. 1 illustrates a diagram showing one example of a device that may benefit from power routing in accordance with an example embodiment.

FIG. 1 illustrates a diagram of a prosthetic limb 100 according to an example embodiment. The prosthetic limb 100 may include a number of joints that can be operated using servomotors or other actuators that require power to operate. Thus, these motors or actuators may be understood to correspond to dynamic loads that are inherently different from each other in some cases based on not only the magnitude of power consumed, but also based on the times and/or frequency of such power consumption. The prosthetic limb 100 may be controlled by electromyography (EMG), where the EMG signals are turned into actuator commands to actuate various joints. In practice, an inference algorithm may be employed to convert the user's EMG signal into an actuator command that provides the limb actuation desired at the appropriate torque. Thus, the inference algorithm may represent an indication of the user's intent relative to operation of the device (and therefore an indication of the expected load that will be generated).

Several of the power consumers or loads are highlighted by dashed ovals in FIG. 1. In this regard, elbow joint 110, wrist joint 120, thumb joint 130 and various finger joints 140 may all be unique in some way. For example, the elbow joint 110 and finger joints 140 may generally only move about a single axis. However, the elbow joint 110 must carry the full weight of the prosthetic limb 100 during operation, and therefore may draw significant amount of power when it operates. Meanwhile, the finger joints 140 may carry much less weight, and therefore may draw less power. The wrist joint 120 may be required to flex in more than one direction, so multiple actuators may be used to operate this joint. Power requirements may vary dependent upon the specific task to be performed such as, for example, turning a key versus opening a jar of pickles.

Various existing types of power sources such as batteries, fuel cells, capacitors, etc., span a wide range of operating characteristics. By employing an example embodiment, information about the available sources, and their corresponding statuses, may be determined. Similarly, the status of loads of the devices being powered may be determined. Thus, information associated with the prosthetic limb 100 that is to be powered, such as the power, total stored energy, durability, weight, and form factor may be used to match available power sources to expectant needs in an efficient way. However, information about sources and loads may be further supplemented with context information to generate intelligent control of power routing to the loads. In example embodiments, the context information should be understood to include intent information and predictive information. The intent information may be indicative of user intent (e.g., the signal generated by the EMG or other such signals such as, for example, electroencephalographic (EEG) signals, eye movement, neural action potential or non-biological commands). Predictive information may include data indicative of historical activity or patterns that may enable informed guesses regarding future activity (or even present activity).

While most existing power management systems take the simple approach of monitoring batteries or other power sources to track power source operating characteristics, example embodiments may further enable dynamic coordination of multiple power source types to meet spatiotemporally varying power demands. Example embodiments may employ microprocessor and sensor feedback to anticipate usage patterns over various timescales in addition to tracking power source operating characteristics.

Figure 2:
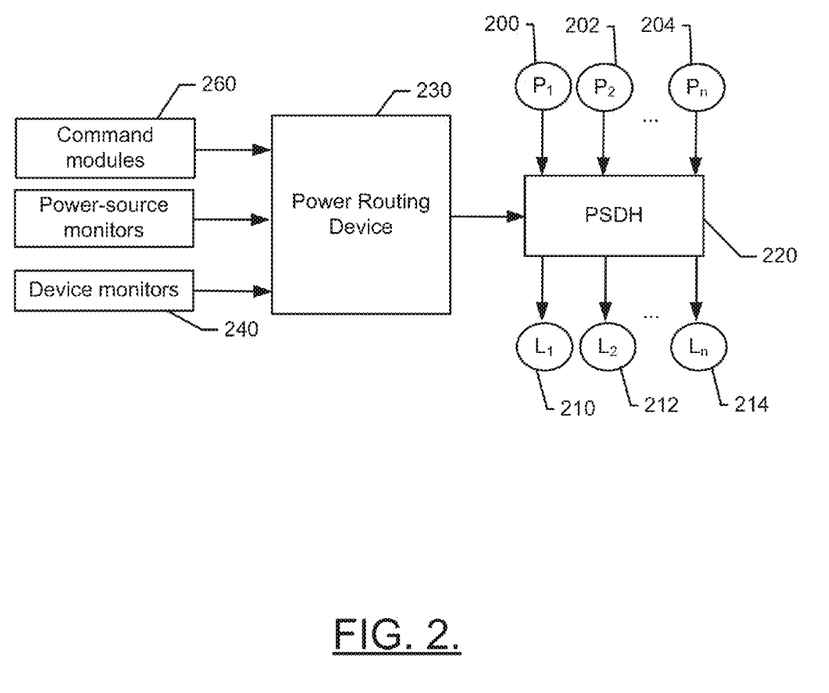
FIG. 2 illustrates a block diagram showing one example of a system for employing power routing in accordance with an example embodiment.

FIG. 2 illustrates a block diagram of a system employing an intelligent power routing device according to an example embodiment. In this regard, as shown in FIG. 2, the system may include a plurality of power sources (e.g., $P_1$ 200, $P_2$ 202, ..., $P_n$ 204) and a plurality of loads (e.g., $L_1$ 210, $L_2$ 212, ..., $L_n$ 214). Some of the power sources may be of different types than others of the power sources, and/or may be provided at different locations. Similarly, some of the loads may be varying loads with different power needs at different times.

Type differences, within the context of example embodiments, may include differences in qualitative and quantitative characteristics of the power source. Thus, for example, size or capacity differences in power sources may define different types of power sources. The nature of the power source may also define a type difference, such that batteries, capacitors, fuel cells, various regulated voltages of different levels, and/or the like, may each define different types. Additionally, AC mains power, hydroelectric power, solar power, wind power, etc., may each define different power source types.

The various loads ($L_1$ 210, $L_2$ 212, ..., $L_n$ 214) may be operably coupled to selected ones of the power sources ($P_1$ 200, $P_2$ 202, ..., $P_n$ 204) through an arrangement such as power source distribution hardware (PSDH) 220. The PSDH 220 mediates the interaction between the loads ($L_1$ 210, $L_2$ 212, ..., $L_n$ 214) and the power sources ($P_1$ 200, $P_2$ 202, ..., $P_n$ 204) via switches, and/or other selectably controllable routes or pathways from the power sources ($P_1$ 200, $P_2$ 202, ..., $P_n$ 204) to the loads ($L_1$ 210, $L_2$ 212, ..., $L_n$ 214). The PSDH 220 may be formed from any suitable combination of components configurable to enable the routing therethrough to be controlled to operably couple selected ones of the power sources ($P_1$ 200, $P_2$ 202, ..., $P_n$ 204) to the loads ($L_1$ 210, $L_2$ 212, ..., $L_n$ 214).

The selectable aspect of the PSDH 220 may allow processing circuitry to interface with the PSDH 220 to control which pathways are established therethrough. In an example embodiment, a power routing device (i.e., an "intelligent" power routing device) 230 may be provided to control the configuration of the PSDH 220. The power routing device 230 may provide instructions to reconfigure the PSDH 220 "intelligently" based on inputs provided thereto, and corresponding programming regarding handling of such inputs. In some cases, the power routing device 230 may be configured to receive an input from device monitors 240 that monitor the loads ($L_1$ 210, $L_2$ 212, ..., $L_n$ 214) and provide information to the power routing device 230 to inform the power routing device 230 of the status of the loads ($L_1$ 210, $L_2$ 212, ..., $L_n$ 214). The power routing device 230 may also be configured to receive an input from power-source monitors 250. The power-source monitors 250 may be configured to monitor the power sources ($P_1$ 200, $P_2$ 202, ..., $P_n$ 204) to provide the power routing device 230 with information indicative of the respective statuses of the power sources ($P_1$ 200, $P_2$ 202, ..., $P_n$ 204). The power routing device 230 may also be configured to receive intent information as described above from command modules 260. The command modules 260 are configured to generate the intent information based on control inputs that define the intent information of the context information. The command modules 260 therefore further enable the power routing device 230 to make the decisions regarding establishing routing through the PSDH 220. As such, the power routing device 230 is configured to provide an output to dynamically coordinate the PSDH 220 contingent upon the inputs from the power-source monitors 250, the device monitors 240 and the command modules 260.

The power-source monitors 250 may monitor each one of the power sources ($P_1$ 200, $P_2$ 202, ..., $P_n$ 204) to determine such operational characteristics as, for example, cell temperature, state-of-charge, balance of stored energy, voltage levels, capacity, etc. The power-source monitors 250 may therefore include temperature sensors, voltage sensors, current sensors, and/or the like. The device monitors 240 may monitor each of the loads ($L_1$ 210, $L_2$ 212, ..., $L_n$ 214) to determine such operational characteristics as, for example, electrical parameters, temperature, pressure, on-off status, location, and/or the like. The device monitors may therefore include electrical sensors, temperature sensors, movement sensors, force sensors, accelerometers, and/or the like. In embodiments where location is determined, the location may sometimes be indicative of a constraint on operation. However, other parameters may also indicate or be associated with a restraint on operation (e.g., temperature, current, etc.).

Figure 3:
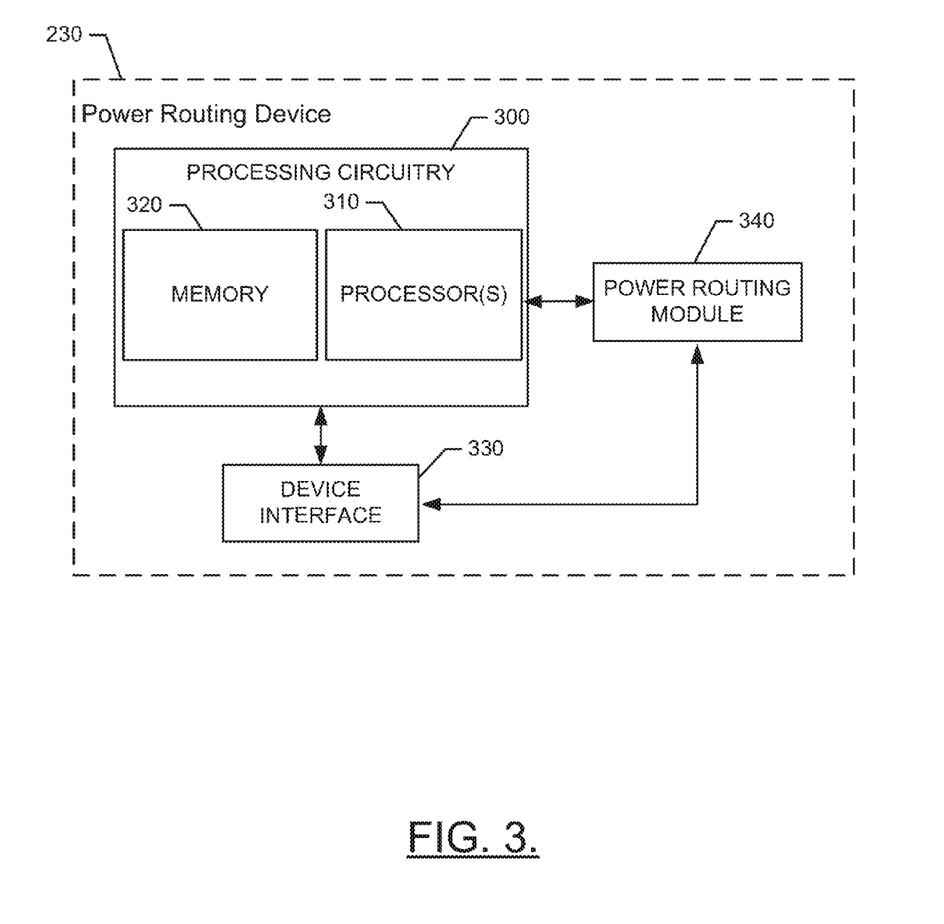
FIG. 3 illustrates a block diagram of a power routing device according to an example embodiment.

The dynamic coordination activities provided by the power routing device 230 may be accomplished via processing circuitry configured to receive the inputs described above and make decisions about power routing based on the inputs received. FIG. 3 illustrates a block diagram of the power routing device 230 of one example embodiment. However, it should be appreciated that the power routing device 230 may take different forms in other example embodiments, so the disclosure and corresponding description of FIG. 3 should be appreciated as corresponding to a single non-limiting example.

As shown in FIG. 3, the power routing device 230 may include or otherwise be in communication with processing circuitry 300 that is configurable to perform actions in accordance with example embodiments described herein. As such, for example, at least some of the functions attributable to the power routing device 230 may be carried out by or otherwise instructed by the processing circuitry 300. The processing circuitry 300 may therefore provide the hardware for hosting software to configure the system for either pre-programmed or machine learning analysis techniques to enable decision making consistent with example embodiments. Processing of input data to determine the optimal power routing for achieving the intent of the user in light of the current status of the loads and available power supplies may then be accomplished using the processing circuitry 300.

The processing circuitry 300 may be configured to perform data processing, control function execution and/or other processing and management services according to an example embodiment of the present invention. In some embodiments, the processing circuitry 300 may be embodied as a chip or chip set. In other words, the processing circuitry 300 may comprise one or more physical packages (e.g., chips) including materials, components and/or wires on a structural assembly (e.g., a baseboard).

In an example embodiment, the processing circuitry 300 may include one or more instances of a processor 310 and memory 320 that may be in communication with or otherwise control a device interface 330. As such, the processing circuitry 300 may be embodied as one or more instances of a circuit chip (e.g., an integrated circuit chip) configured (e.g., with hardware, software or a combination of hardware and software) to perform operations described herein.

The device interface 330 may include one or more interface mechanisms for enabling communication with other external devices (e.g., output devices, input devices and/or the like) or internal functional components of the detection system. In some cases, the device interface 330 may be any means such as a device or circuitry embodied in either hardware, or a combination of hardware and software that is configured to receive and/or transmit data from/to devices in communication with the processing circuitry 300.

In an exemplary embodiment, the memory 320 may include one or more non-transitory memory devices such as, for example, volatile and/or non-volatile memory that may be either fixed or removable. The memory 320 may be configured to store information, data, applications, instructions or the like for enabling the power routing device 230 to carry out various functions in accordance with exemplary embodiments of the present invention. For example, the memory 320 could be configured to buffer input data for processing by the processor 310. Additionally or alternatively, the memory 320 could be configured to store instructions for execution by the processor 310. As yet another alternative, the memory 320 may include one or more databases that may store a variety of data sets indicative of operating patterns, schedule data, priority rankings for loads and/or power supplies, processing algorithms and/or the like to be employed for the execution of example embodiments. Among the contents of the memory 320, applications may be stored for execution by the processor 310 in order to carry out the functionality associated with each respective application. In some cases, the applications may include directions for control of the power routing device 230 to process information regarding load status, power-source status, and context information as described above. Thus, an application may be provided for routing of power to the loads considering the status of both the loads and power supplies available, but further in consideration of intent information and predictive information (i.e., context information). In some cases, the applications may further include directions for generating one or more reports associated with analysis of power routing for further study or use as predictive information as described herein.

The processor 310 (or processors) may be embodied in a number of different ways. For example, the processor 310 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 310 may be configured to execute instructions stored in the memory 320 or otherwise accessible to the processor 310. As such, whether configured by hardware or by a combination of hardware and software, the processor 310 may represent an entity (e.g., physically embodied in circuitry—in the form of processing circuitry 300) capable of performing operations according to embodiments of the present invention while configured accordingly. Thus, for example, when the processor 310 is embodied as an ASIC, FPGA or the like, the processor 310 may be specifically configured hardware for conducting the operations described herein. Alternatively, as another example, when the processor 310 is embodied as an executor of software instructions, the instructions may specifically configure the processor 310 to perform the operations described herein.

In an example embodiment, the processor 310 (or the processing circuitry 300) may be embodied as, include or otherwise control a power routing module 340. As such, in some embodiments, the processor 310 (or the processing circuitry 300) may be said to cause each of the operations described in connection with the power routing module 340 to undertake the corresponding functionalities responsive to execution of instructions or algorithms configuring the processor 310 (or processing circuitry 300) accordingly.

In an example embodiment, the power routing module 340 may include or identify information descriptive of the characteristics of each of the power sources ($P_1$ 200, $P_2$ 202, . . . , $P_n$ 204) and each of the loads ($L_1$ 210, $L_2$ 212, . . . , $L_n$ 214). As such, the power routing module 340 may have knowledge of the ratings, capacities, and/or other information descriptive of each of the power sources ($P_1$ 200, $P_2$ 202, . . . , $P_n$ 204) and each of the loads ($L_1$ 210, $L_2$ 212, . . . , $L_n$ 214). In some cases, the power routing module 340 may further include information descriptive of a priority rating or other indication of importance or the degree to which specific ones of the loads ($L_1$ 210, $L_2$ 212, . . . , $L_n$ 214) are considered vital. The priority rating may be used to favor distribution of power to selected ones of the loads ($L_1$ 210, $L_2$ 212, . . . , $L_n$ 214) when available power supply does not meet the demands of the loads ($L_1$ 210, $L_2$ 212, . . . , $L_n$ 214).

The power routing module 340 may alternatively or additionally include information about the nature of various ones of the loads ($L_1$ 210, $L_2$ 212, . . . , $L_n$ 214). Thus, for example, the power routing module 340 may include information indicative of whether certain ones of the loads ($L_1$ 210, $L_2$ 212, . . . , $L_n$ 214) are cycling loads, steady loads, and whether there are any known patterns of operation of such loads. Patterns of operation may include information indicating that the loads are inoperative at night (e.g., when the wearer of a prosthesis is sleeping), or that the loads typically operate in a specific way during certain periods of time or activity. The patterns and/or other historical information about the loads may form a portion of the context information that is used by the power routing module 340 to make routing decisions as described herein.

In some example embodiments, the power routing module 340 may further include information about the nature of various ones of the power sources ($P_1$ 200, $P_2$ 202, . . . , $P_n$ 204). For example, the power routing module 340 may include information indicating that specific ones of the power sources ($P_1$ 200, $P_2$ 202, . . . , $P_n$ 204) are rechargeable, and the time it takes to recharge such power sources ($P_1$ 200, $P_2$ 202, . . . , $P_n$ 204) nominally and/or under specific circumstances. Historical information, or information regarding patterns regarding charging of the power sources ($P_1$ 200, $P_2$ 202, . . . , $P_n$ 204) may also form a portion of the context information used by the power routing module 340 to make routing decisions as described herein.

As discussed above, the power routing module 340 may also receive dynamic information indicative of current status of the power sources ($P_1$ 200, $P_2$ 202, . . . , $P_n$ 204) and the loads ($L_1$ 210, $L_2$ 212, . . . , $L_n$ 214) from the power-source monitors 250 and the device monitors 240, respectively. This dynamic information on device and source status is coupled with context information to make routing decisions. The context information, as described above, includes intent information from the command modules 260, but also includes predictive information based on patterns or historical information that may be stored or otherwise known by the power routing module 340.

In an example embodiment, the power routing module 340 may employ a decision tree identifying a step-wise decision making procedure for the power routing module 340 to follow relative to deciding which ones of the power sources ($P_1$ 200, $P_2$ 202, . . . , $P_n$ 204) to route for powering respective ones of the loads ($L_1$ 210, $L_2$ 212, . . . , $L_n$ 214).

The decision tree may consider priority information, as mentioned above. However, the decision tree may also consider matching power requirements to corresponding available sources that most closely match the power requirements. For example, if a particular load is expected to be cycled repeatedly over the next two hours, the power routing module 340 may be configured to select a source that has more than two hours of capacity relative to powering loads of the size of the particular load. Thus, the decision tree may consider the total expected power requirement over a given period of time at a given rate of power consumption, and further consider the time for which each power source that can meet the need at the given rate when deciding which source to route to the corresponding load. If one source is capable of meeting the total expected power requirement over the given period of time, the one source may be routed to power the corresponding load. However, if the one source can only cover a portion of the given period of time, then multiple sources may be lined up to meet the need. The power routing module 340 may, in some cases, define a power routing schedule that identifies a schedule for connection of specific ones of the power sources ($P_1$ 200, $P_2$ 202, ..., $P_n$ 204) to respective ones of the loads ($L_1$ 210, $L_2$ 212, ..., $L_n$ 214) for a given period of time.

In any case, after the power routing module 340 makes power routing decisions, the power routing module 340 may enable the power routing device 230 to use the corresponding decisions to provide inputs to the PSDH 220 to make the corresponding routing connections. The routing connections may be made while device status and power source status information continues to be monitored. Thus, if any changes are noted that require changes to any schedule or routing decision that was previously made, the power routing module 340 may be configured to be responsive to the feedback received during operation to make any necessary changes. The routing connections can be made and changed by operation of switches or other such components associated with any hardware routing assembly that one of skill in the art may choose to employ for the PSDH 220. However, one example of circuitry that may be employed in accordance with some embodiments is shown in FIG. 4.

Figure 4:
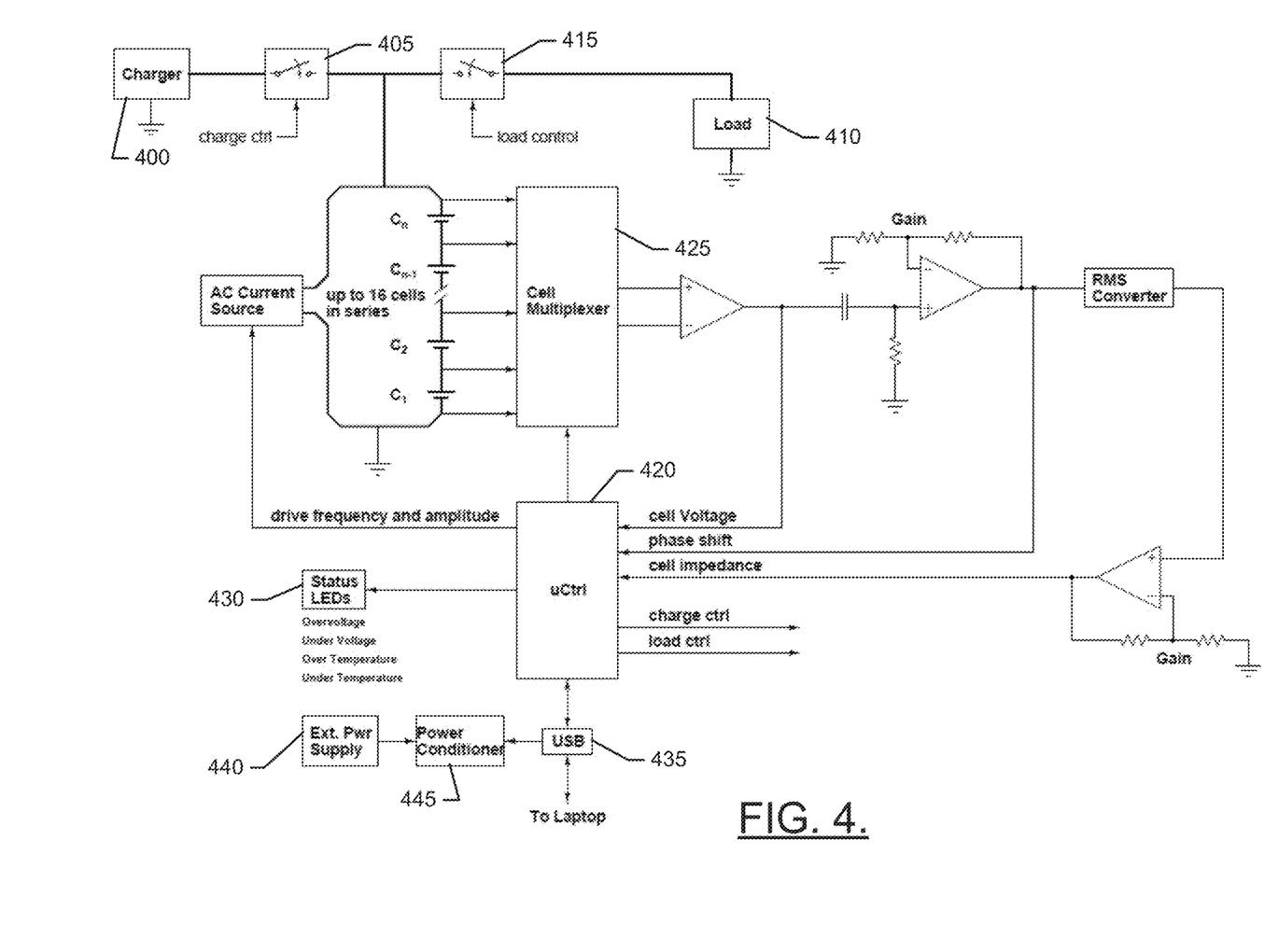
FIG. 4 shows a block diagram of circuitry for providing power routing according to an example embodiment.

As shown in FIG. 4, a charger 400 may be provided to charge a plurality of cells (e.g., $C_1$, $C_2$, ..., $C_{n-1}$, $C_n$, which may be rechargeable battery cells or capacitors in some alternatives). The charger 400 may be isolated from the cells ($C_1$, $C_2$, ..., $C_{n-1}$, $C_n$) via a charge control switch 405. One or more instances of a load 410 may also be connectable to the cells ($C_1$, $C_2$, ..., $C_{n-1}$, $C_n$) by operation of a load control switch 415. A microcontroller 420 (e.g., an instance of portion of the power routing device 230) may interface with a cell multiplexor 425 to monitor one or more of the outputs of the cells ($C_1$, $C_2$, ..., $C_{n-1}$, $C_n$) for cell voltage, phase shift and impedance to make decisions regarding operation of the charge control switch 405 and the load control switch 415 to ensure that the load 410 is powered appropriately. In some cases, the microcontroller 420 may also provide status information (e.g., via status LEDs 430) to indicate various conditions of the cells and/or loads. Control or interface with the microcontroller 420 may be accomplished from an external laptop via a USB connection 435, and an external power source 440 may provide power to a power conditioner 445, which may also interface with the microcontroller 420 via the USB connection 435.

As mentioned above, the power routing module 340 may make routing decisions dynamically based on changing conditions regarding the load and the power sources. One such changing condition may be the temperature of the cells of any battery sources used. Battery charging and discharging may increase cell temperature, and cell overheating can damage battery cells. As such, cell overheating must be avoided. To accomplish such avoidance, the power routing module 340 may further be configured to change routing decisions based on cell temperature. In some embodiments, battery cell temperature may be monitored by a battery internal temperature sensor. Thus, the power routing module 340 may use information on cell voltage, state-of-charge, state of health of the battery, internal resistance (from the battery internal temperature sensor) and other sources in order to intelligently route power. Intelligent power routing therefore not only matches the most suitable source to each load based on the ability to simply provide the needed power, but also in a way that protects the health and safety of the power sources.

Of note, the power routing decisions can be made in parallel with each other, and in parallel with the gathering or receipt of information upon which the decisions are made. Thus, the power routing module 340 can resolve and execute multiple requests or processing operations in parallel and substantially in real time. However, sequential operation and processing is also possible in some embodiments.

Figure 5:
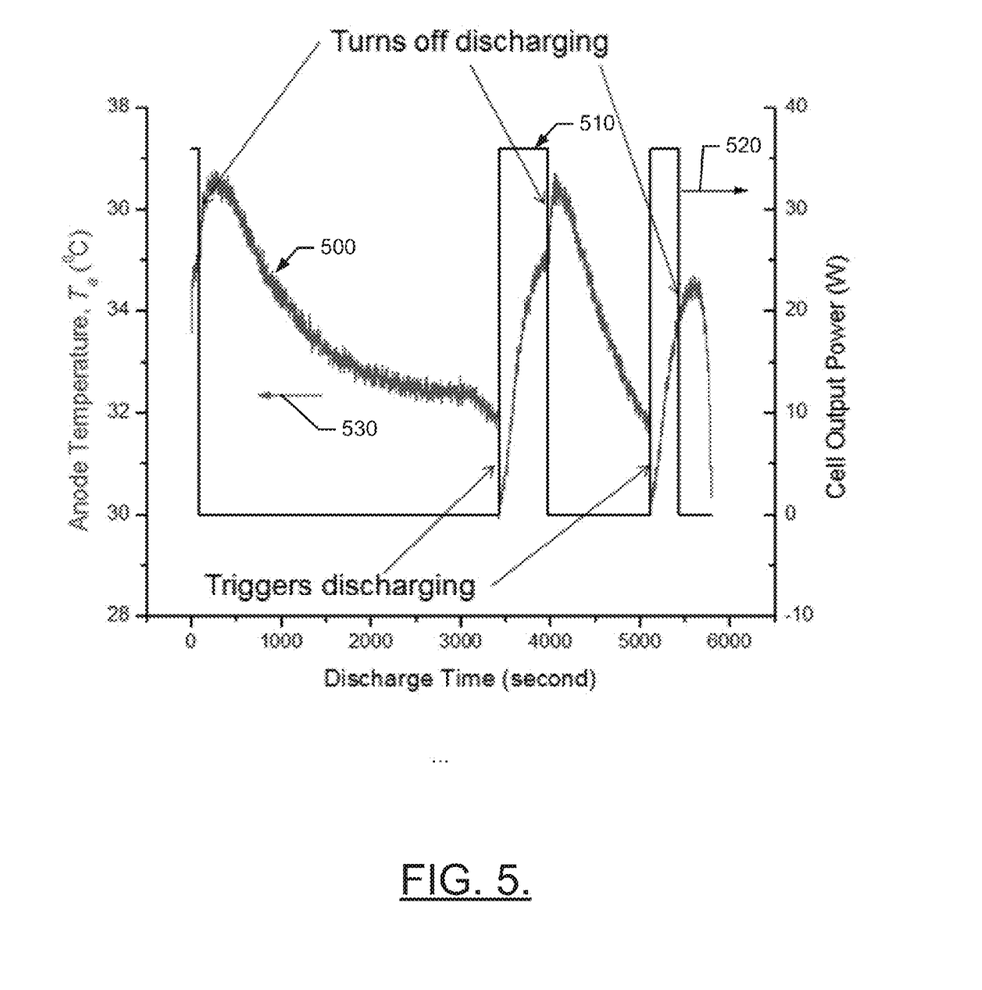
FIG. 5 illustrates a diagram of cell output power and internal temperature versus time to show operation of a power routing device to control cell discharge according to an example embodiment.

FIG. 5 illustrates an example power control diagram associated with operation of an example embodiment. In this regard, FIG. 5 illustrates a display of cell internal temperature 500 and cell output power 510 versus time. FIG. 5 also illustrates a shutoff temperature threshold 520 and a reset temperature 530. The cell may discharge (as shown by the curve for cell output power 510) and cause cell temperature to rise (as shown by the curve for cell internal temperature 500) during discharge, as expected. When the cell temperature exceeds the shutoff temperature threshold 520, cell discharging may be turned off by the power routing module 340. If the load needs continued power, the power routing module 340 may define another source and the power routing device 230 may interact with the PSDH 220 to provide the alternate routing needed to supply the continued power to the load. When cell temperature reaches the safety of reset temperature 530, a determination may be made as to whether to switch powering of the load back to this cell or whether to power another load. In any case, when the power routing module 340 needs power, discharging may again be allowed until cell temperature exceeds the shutoff temperature threshold 520 again.

Example embodiments may therefore provide for an intelligent power routing capability. In the context of a prosthetic device, periods of inactivity and the intent of the user relative to the task to be performed may allow the power routing device 230 (e.g., via decisions made by the power routing module 340) to strategically and intelligently select power sources to match the specific individual loads of the prosthetic limb 100. Small loads may be powered from small power supplies, and large loads may be powered from larger capacity power supplies. However, cell temperature, state of charge and other factors may also be considered to efficiently and effectively ensure optimal power provision in a potentially dynamic environment.

Although powering different loads of the prosthetic limb 100 has been described as one example of operation of an example embodiment, the power routing device 230 may also work in other contexts. For example, the power routing device 230 could also be used in the context of a vehicle, robot, or other device having loads that range in size from small to large, and potentially also have different use patterns or routines, along with multiple power sources from which the loads can be powered. Autonomous cars and electric vehicles (EV) have stratified power demands for operating, for example, GPS, controls and propulsion. Similar analogies are found inside a typical home where light bulbs to heating systems that demand a few watts to several kilowatts of power, depending upon the time of the day, can be found. Even though the prevalence of wide-ranging power demands within individual systems have been long recognized, the power system design has not been the priority of systems design engineers and architects. As the demand for EVs, self-driving cars, robots and smart-power homes increases, architects may be forced to alleviate range-anxiety in cars, power loss in robots and brown outs in homes. The mundane approach of power-all-with-single-source in modern EVs, for example, will become obsolete as the regulations take hold to prevent driving a car with a damaged battery. Functions of a robot or a home may be different from an EV, but the consequences of failure of a power-all-with-single-source philosophy are not.

Figure 6:
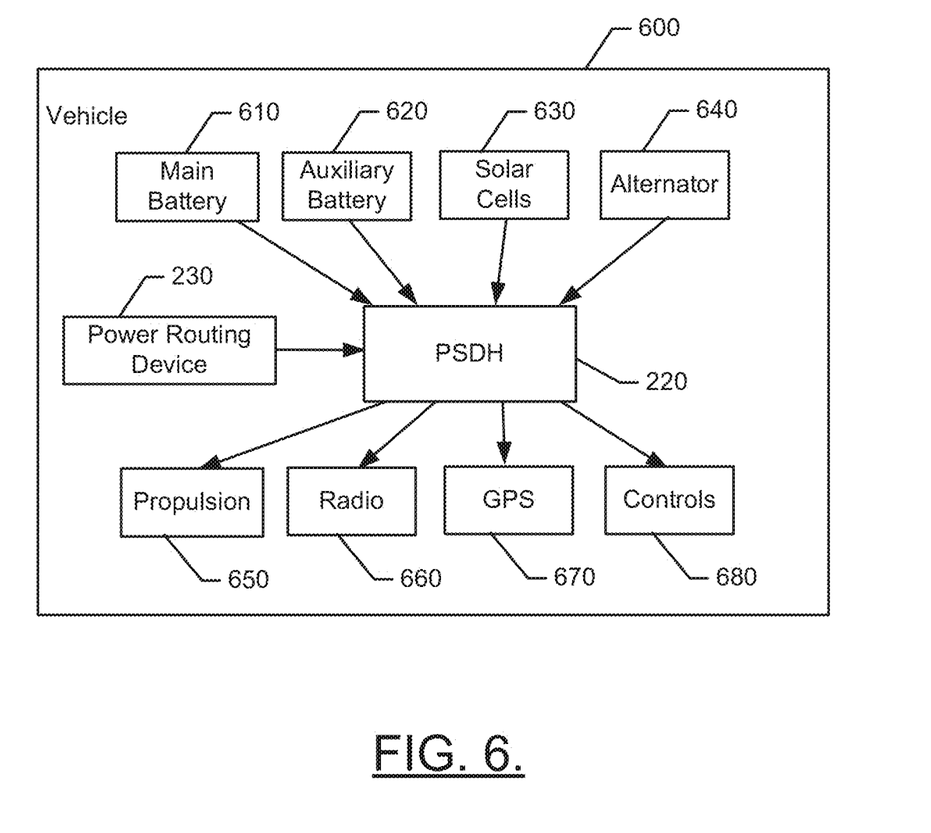
FIG. 6 illustrates a block diagram showing one example of a vehicle employing power routing in accordance with an example embodiment.

FIG. 6 illustrates an example in which a device having stratified power demands based on having a wide range of load requirements is illustrated in the form of a vehicle. As shown in FIG. 6, the vehicle 600 may include multiple types of power sources such as, for example, a main battery 610, an auxiliary battery 620, solar cells 630 and an alternator 640. However, it should be appreciated that additional or alternative power sources may be included in some alternative embodiments. The vehicle 600 may also include various different types of loads such as, for example, a propulsion load 650 (e.g., electric motor), radio 660, GPS system 670, and various components associated with vehicle controls 680. However, it should be appreciated that additional or alternative loads may be included in some alternative embodiments. As described above, the power routing device 230 may receive the inputs described in reference to FIG. 2, and control the routing of power from the power sources to the loads via the PSDH 220. In the context of a vehicle with multiple different power sources and loads, context information may include information about speed limits in given areas, or traffic jams, so that inferences can be made regarding the likely speed that the operator will request based on the context information. In such an example, the location may indicate a constraint upon operation. Power routing can therefore consider predictive information as described above.

Figure 7:
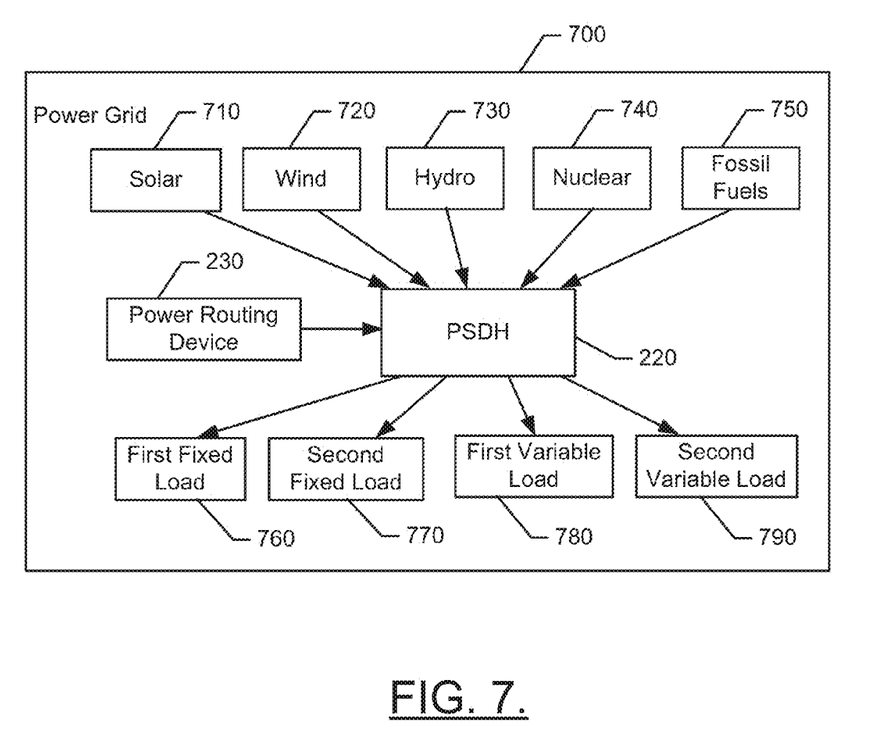
FIG. 7 illustrates a block diagram showing one example of a power grid employing power routing in accordance with an example embodiment.

FIG. 7 illustrates an example in which a device having stratified power demands based on having a wide range of load requirements is illustrated in the form of a power grid. For example, power routing in accordance with example embodiments could be used for power grid management decisions balancing different types of power sources (e.g., solar 710, wind 720, hydro 730, nuclear 740, fossil fuel 750, etc.) to power various loads of a power grid 700. The loads may include fixed loads (e.g., first fixed load 760 and second fixed load 770) and variable loads (e.g., first variable load 780 and second variable load 790), and the power routing device 230 may receive the inputs described in reference to FIG. 2 and control the routing of power from the power sources to the loads via the PSDH 220 to match available power sources to required power needs with, in some cases, priorities defined to minimize cost and/or environmental impact. Some example embodiments could also be employed in the context of uninterruptable power supplies, where each outlet powers a different load, and decisions can be made as to segmentation of the battery backup into cells to power respective ones of the loads while other cells are charged. Still other examples and use cases will also become apparent to one of skill in the art.

Many modifications and other embodiments of the invention set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A power routing system comprising:
a plurality of loads including a first load and a second load, at least some of the loads having different operational characteristics than other ones of the loads;
a plurality of power sources, at least some of the power sources having different operational characteristics than other ones of the power sources, the plurality of power sources including a battery;
power-source distribution hardware selectively operably coupling selected ones of the power sources to selected ones of the loads;
device monitors configured to determine load status information from the loads;
power-source monitors configured to determine source status information from the power sources, the source status information for the battery including an internal cell temperature of a battery cell;
command modules configured to provide context information regarding the loads or the power sources; and
a power routing device operably coupled to the command modules, the power-source monitors and the device monitors, the power routing device being configured to receive the source status information, the load status information and the context information and to direct the power-source distribution hardware to define routing between the selected ones of the power sources and the selected ones of the loads based on the source status information, the load status information and the context information;
wherein the power routing device is configured to:
in response to the internal cell temperature exceeding a shutoff temperature threshold, change routing to discontinue powering the first load from the battery; and
in response to the internal cell temperature subsequently reaching a reset temperature threshold, change routing to power the second load from the battery based on the source status information, the load status information and the context information.

2. The power routing system of claim 1, wherein the context information comprises intent information indicative of user intent for operation of a load.

3. The power routing system of claim 2, wherein the loads are components of a prosthetic limb and the intent information is determined from electromyography (EMG) signals, electroencephalographic (EEG) signals, eye movement, neural action potential or non-biological commands.

4. The power routing system of claim 1, wherein the context information comprises predictive information.

5. The power routing system of claim 4, wherein the predictive information defines historical power requirements or a pattern of activity for a load.

6. The power routing system of claim 5, wherein the predictive information is stored in memory accessible by the power routing device, and wherein an instance of the predictive information is defined for each one of the loads.

7. The power routing system of claim 4, wherein the predictive information defines information associated with a location of operation of a load, and wherein the location of operation relates to a constraint on operation of the load.

8. The power routing system of claim 1, wherein the power routing device stores information indicative of state-of-charge and battery health for at least some of the power sources.

9. The power routing system of claim 8, wherein the power routing device is configured to selectively change routing based on the state-of-charge and battery health.

10. A power routing device comprising:
processing circuitry configured to receive inputs from:
device monitors configured to determine load status information from a plurality of loads including a first load and a second load, at least some of the loads having different operational characteristics than other ones of the loads,
power-source monitors configured to determine source status information from a plurality of power sources including a first source, at least some of the power sources having different operational characteristics than other ones of the power sources, the source status information including an internal resistance of the first source, and
command modules configured to provide context information regarding the loads or the power sources,
wherein the power routing device is operably coupled to power-source distribution hardware selectively operably coupling selected ones of the power sources to selected ones of the loads, and
wherein the power routing device is configured to direct the power-source distribution hardware to define routing between the selected ones of the power sources and the selected ones of the loads based on the source status information, the load status information and the context information;
wherein the power routing device is configured to change routing, based on the internal resistance, to discontinue powering the first load from the first source and power the second load from the first source.

11. The power routing device of claim 10, wherein the context information comprises intent information indicative of user intent for operation of a load.

12. The power routing device of claim 11, wherein the loads are components of a prosthetic limb and the intent information is determined from electromyography (EMG) signals, electroencephalographic (EEG) signals, eye movement, neural action potential or non-biological commands.

13. The power routing device of claim 10, wherein the context information comprises predictive information.

14. The power routing device of claim 13, wherein the predictive information defines historical power requirements or a pattern of activity for a load.

15. The power routing device of claim 14, wherein the predictive information is stored in memory accessible by the power routing device, and wherein an instance of the predictive information is defined for each one of the loads.

16. The power routing device of claim 13, wherein the predictive information defines information associated with a location of operation of a load, and wherein the location of operation relates to a constraint on operation of the load.

17. The power routing device of claim 10, wherein the source status information includes dynamic information regarding internal cell temperature of a battery cell.

18. The power routing device of claim 10, wherein the power routing device stores information indicative of cell voltage, state-of-charge and battery health for at least some of the power sources.

19. A method comprising:
receiving, at a power routing device, load status information associated with a plurality of loads from device monitors operably coupled to the plurality of loads, at least some of the loads having different operational characteristics than other ones of the loads, the plurality of loads including a first load and a second load;
receiving, at the power routing device, source status information associated with a plurality of power sources from power-source monitors operably coupled to the plurality of power sources, at least some of the power sources having different operational characteristics than other ones of the power sources, the plurality of power sources including a battery, and the source status information for the battery including an internal cell temperature of a battery cell; and
directing, by the power outing device, a power-source distribution hardware to define routing between selected ones of the power sources and selected ones of the loads based on the source status information and the load status information;
wherein directing the power-source distribution hardware to define routing comprises:
in response to the internal cell temperature exceeding a shutoff temperature threshold, changing routing to discontinue powering the first load from the battery; and
in response to the internal cell temperature subsequently reaching a reset temperature threshold, changing routing to power the second load from the battery based on the source status information and the load status information.

* * * * *